United States Patent [19]

Sih

[11] 4,259,528
[45] Mar. 31, 1981

[54] 2-DECARBOXY-2-HYDROXYMETHYL-19,20-DIDEHYDRO-PG₁ COMPOUNDS

[75] Inventor: John C. Sih, Kalamazoo, Mich.

[73] Assignee: The Upjohn Company, Kalamazoo, Mich.

[21] Appl. No.: 85,625

[22] Filed: Oct. 17, 1979

Related U.S. Application Data

[62] Division of Ser. No. 26,066, Apr. 2, 1979.

[51] Int. Cl.³ .......................................... C07C 177/00
[52] U.S. Cl. .................................. 568/379; 568/330; 568/646; 568/670; 568/807; 568/838

[58] Field of Search ...................... 260/580 R, 590 C; 568/646, 670, 838, 807, 330, 379

[56] References Cited

FOREIGN PATENT DOCUMENTS 2635985 2/1978 Fed. Rep. of Germany .

Primary Examiner—Robert Gerstl
Attorney, Agent, or Firm—Robert A. Armitage

[57] ABSTRACT

The present invention provides novel 2-decarboxy-2-hydroxymethyl-19,20-didehydro-PG₁ compounds, methods for their preparation and pharmacological use for the induction of prostaglandin-like effect.

67 Claims, No Drawings

2-DECARBOXY-2-HYDROXYMETHYL-19,20-DIDEHYDRO-PG₁ COMPOUNDS

CROSS REFERENCE TO RELATED APPLICATIONS

The present application is a division of Ser. No. 026,066, filed Apr. 2, 1979 pending issuance as a United States Patent.

BACKGROUND OF THE INVENTION

The present invention relates to novel prostaglandin analogs. Particularly, these compounds are analogs of the prostaglandins wherein the C-20-C-19 position is unsaturated. i.e., 19,20-didehydro-PG compounds. Most particularly, the present invention relates to novel 2-decarboxy-2-hydroxymethyl-19,20-didehydro-PG$_1$ compounds, a disclosure of the preparation and use of which is incorporated here by reference from U.S. Pat. No. 4,228,104.

Prior Art

Prostaglandin analogs exhibiting unsaturation in the C-17, C-18, or C-20 position are known in the art. See, for example, U.S. Pat. No. 3,919,285 German Offenlegungsschrift No. 2,635,985 (and its corresponding Derwent Farmdoc CPI No. 10302A), and U.S. Pat. No. 4,064,351 for examples of such compounds. See also the references cited in U.S. Ser. No. 026.066.

SUMMARY OF THE INVENTION

The present invention particularly provides:
A compound of the formula

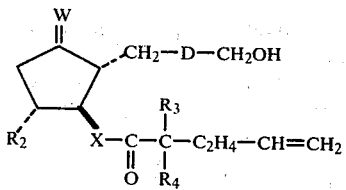

wherein D is
(1) —(CH$_2$)$_3$—(CH$_2$)$_g$—CH$_2$—,
(2) —(CH$_2$)$_3$—CH$_2$—CF$_2$—,
(3) —(CH$_2$)$_3$—O—CH$_2$—,
(4) —(CH$_2$)$_2$—O—(CH$_2$)$_2$—,
(5) —CH$_2$—O—(CH$_2$)$_3$—, (6) 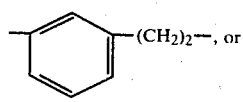 —(CH$_2$)$_2$—, or (7) 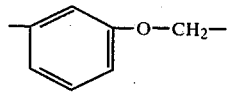 —O—CH$_2$— wherein g is zero, one, two, or three;
wherein Q is

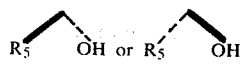

wherein R$_5$ is hydrogen or methyl, wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is

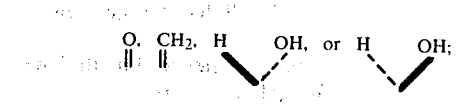

and wherein X is cis- or trans-CH=CH— or —C≡C—.

Specific embodiments of the present invention include
2-decarboxy-2-hydroxymethyl-19,20-didehydro-PGF$_{1\alpha}$,
2-decarboxy-2-hydroxymethyl-16,16-dimethyl-19,20-didehydro-PGF$_{1\alpha}$,
2-decarboxy-2-hydroxymethyl-16,16-difluoro-19,20-didehydro-PGF$_{1\alpha}$,
2-decarboxy-2-hydroxymethyl-11-deoxy-19,20-didehydro-PGF$_{1\alpha}$,
2-decarboxy-2-hydroxymethyl-11-deoxy-16,16-dimethyl-19,20-didehydro-PGF$_{1\alpha}$,
2-decarboxy-2-hydroxymethyl-11-deoxy-16,16-difluoro-19,20-didehydro-PGF$_{1\alpha}$,
2-decarboxy-2-hydroxymethyl-11-deoxy-11$\alpha$-hydroxymethyl-19,20-didehydro-PGF$_{1\alpha}$,
2-decarboxy-2-hydroxymethyl-11-deoxy-11$\alpha$-hydroxymethyl-16,16-dimethyl-19,20-didehydro-PGF$_{1\alpha}$,
2-decarboxy-2-hydroxymethyl-11-deoxy-11$\alpha$-hydroxymethyl-16,16-difluoro-19,20-didehydro-PGF$_{1\alpha}$,
2-decarboxy-2-hydroxymethyl-19,20-didehydro-PGF$_{1\alpha}$,
2-decarboxy-2-hydroxymethyl-16,16-dimethyl-19,20-didehydro-PGF$_{1\beta}$,
2-decarboxy-2-hydroxymethyl-16,16-difluoro-19,20-didehydro-PGF$_{1\beta}$,
2-decarboxy-2-hydroxymethyl-11-deoxy-19,20-didehydro-PGF$_{1\beta}$,
2-decarboxy-2-hydroxymethyl-11-deoxy-16,16-dimethyl-19,20-didehydro-PGF$_{1\beta}$,
2-decarboxy-2-hydroxymethyl-16,16-difluoro-19,20-didehydro-PGF$_{1\beta}$,
2-decarboxy-2-hydroxymethyl-11-deoxy-11$\alpha$-hydroxymethyl-19,20-didehydro-PGF$_{1\beta}$,
2-decarboxy-2-hydroxymethyl-11-deoxy-11$\alpha$-hydroxymethyl-16,16-dimethyl-19,20-didehydro-PGF$_{1\beta}$,
2-decarboxy-2-hydroxymethyl-11-deoxy-11$\alpha$-hydroxymethyl-16,16-difluoro-19,20-didehydro-PGF$_{1\beta}$,
2-decarboxy-2-hydroxymethyl-19,20-didehydro-PGE$_1$,
2-decarboxy-2-hydroxymethyl-16,16-dimethyl-19,20-didehydro-PGE$_1$,
2-decarboxy-2-hydroxymethyl-16,16-difluoro-19,20-dihydro-PGE$_1$,
2-decarboxy-2-hydroxymethyl-11-deoxy-19,20-didehydro-PGE$_1$,
2-decarboxy-2-hydroxymethyl-11-deoxy-16,16-dimethyl-19,20-didehydro-PGE$_1$,
2-decarboxy-2-hydroxymethyl-11-deoxy-16,16-difluoro-19,20-didehydro-PGE$_1$,
2-decarboxy-2-hydroxymethyl-11-deoxy-11$\alpha$-hydroxymethyl-19,20-didehydro-PGE$_1$, 2-decarboxy-2-hydroxymethyl-11-deoxy-11α-
  hydroxymethyl-16,16-dimethyl-19,20-didehydro-
  PGE$_1$,
2-decarboxy-2-hydroxymethyl-11-deoxy-11α-
  hydroxymethyl-16,16-difluoro-19,20-didehydro-
  PGE$_1$,
2-decarboxy-2-hydroxymethyl-9-deoxo-9-methylene-
  19,20-didehydro-PGE$_1$,
2-decarboxy-2-hydroxymethyl-9-deoxo-9-methylene-
  16,16-dimethyl-19,20-didehydro-PGE$_1$,
2-decarboxy-2-hydroxymethyl-9-deoxo-9-methylene-
  16,16-difluoro-19,20-didehydro-PGE$_1$,
2-decarboxy-2-hydroxymethyl-9-deoxo-9-methylene-
  11-deoxy-19,20-didehydro-PGE$_1$,
2-decarboxy-2-hydroxymethyl-9-deoxo-9-methylene-
  11-deoxy-16,16-dimethyl-19,20-didehydro-PGE$_1$,
2-decarboxy-2-hydroxymethyl-9-deoxo-9-methylene-
  11-deoxy-16,16-difluoro-19,20-didehydro-PGE$_1$,
2-decarboxy-2-hydroxymethyl-9-deoxo-9-methylene-
  11-deoxy-11α-hydroxymethyl-19,20-didehydro-
  PGE$_1$,
2-decarboxy-2-hydroxymethyl-9-deoxo-9-methylene-
  11-deoxy-11α-hydroxymethyl-16,16-dimethyl-
  19,20-didehydro-PGE$_1$,
2-decarboxy-2-hydroxymethyl-9-deoxo-9-methylene-
  11-deoxy-11α-hydroxymethyl-16,16-difluoro-
  19,20-didehydro-PGE$_1$.

The compounds of the present invention are particularly useful for inducing prostaglandin-like biological effects, as is described in U.S. Ser. No. 026,066. Uses of compounds in accordance with the present invention include, therefore, anti-asthmatic indication.

I claim:
1. A compound of the formula

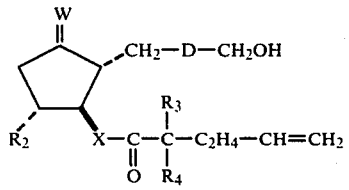

wherein D is
(1) —(CH$_2$)$_3$—(CH$_2$)$_g$—CH$_2$—,
(2) —(CH$_2$)$_3$—CH$_2$—CF$_2$—,
(3) —(CH$_2$)$_3$—O—CH$_2$—,
(4) —(CH$_2$)$_2$—O—(CH$_2$)$_2$—,
(5) —CH$_2$—O—(CH$_2$)$_3$—,

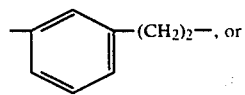 (6)

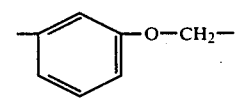 (7)

wherein g is zero, one, two, or three;
wherein Q is

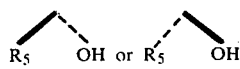

wherein R$_5$ is hydrogen or methyl, wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is

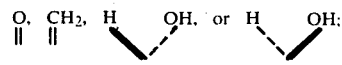

and wherein X is cis- or trans-CH=CH— or —C≡C—.

2. A compound according to claim 1, wherein D is -(CH$_2$)$_3$-(CH$_2$)$_g$-CH$_2$-, wherein g is zero, one, two or three.

3. A compound according to claim 2, wherein g is one.

4. A compound according to claim 3, wherein W is

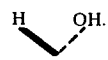

5. A compound according to claim 4, wherein R$_2$ is hydroxyl.

6. A compound according to claim 5, wherein X is trans-CH=CH-.

7. 2-Decarboxy-2-hydroxymethyl-19,20-didehydro-PGF$_{1α}$, a compound according to claim 6.

8. 2-Decarboxy-2-hydroxymethyl-16,16-dimethyl-19,20-didehydro-PGF$_{1α}$, a compound according to claim 6.

9. 2-Decarboxy-2-hydroxymethyl-16,16-difluoro-19,20-didehydro-PGF$_{1α}$, a compound according to claim 6.

10. A compound according to claim 4, wherein R$_2$ is hydrogen.

11. A compound according to claim 10, wherein X is trans-CH=CH-.

12. 2-Decarboxy-2-hydroxymethyl-11-deoxy-19,20-didehydro-PGF$_{1α}$, a compound according to claim 11.

13. 2-Decarboxy-2-hydroxymethyl-11-deoxy-16,16-dimethyl-19,20-didehydro-PGF$_{1α}$, a compound according to claim 11.

14. 2-Decarboxy-2-hydroxymethyl-11-deoxy-16,16-difluoro-19,20-didehydro-PGF$_{1α}$, a compound according to claim 11.

15. A compound according to claim 4, where R$_2$ is hydroxymethyl.

16. A compound according to claim 15, wherein X is trans-CH=CH-.

17. 2-Decarboxy-2-hydroxymethyl-11-deoxy-11α-hydroxymethyl-19,20-didehydro-PGF$_{1α}$, a compound according to claim 15.

18. 2-Decarboxy-2-hydroxymethyl-11-deoxy-11α-hydroxymethyl-16,16-dimethyl-19,20-didehydro-PGF$_{1α}$, a compound according to claim 15.

19. 2-Decarboxy-2-hydroxymethyl-11-deoxy-11α-hydroxymethyl-16,16-difluoro-19,20-didehydro-PGF$_{1α}$, a compound according to claim 15.

20. A compound according to claim 3, wherein W is

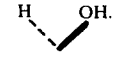

21. A compound according to claim 20, wherein R$_2$ is hydroxyl.

22. A compound according to claim 21, wherein X is trans-CH=CH-.

23. 2-Decarboxy-2-hydroxymethyl-19,20-didehydro-PGF$_{1\beta}$, a compound according to claim 22.

24. 2-Decarboxy-2-hydroxymethyl-16,16-dimethyl-19,20-didehydro-PGF$_{1\beta}$, a compound according to claim 20.

25. 2-Decarboxy-2-hydroxymethyl-16,16-difluoro-19,20-didehydro-PGF$_{1\beta}$, a compound according to claim 22.

26. A compound according to claim 20, wherein R$_2$ is hydrogen.

27. A compound according to claim 26, wherein X is trans-CH=CH-.

28. 2-Decarboxy-2-hydroxymethyl-11-deoxy-19,20-didehydro-PGF$_{1\beta}$, a compound according to claim 27.

29. 2-Decarboxy-2-hydroxymethyl-11-deoxy-16,16-dimethyl-19,20-didehydro-PGF$_{1\beta}$, a compound according to claim 27.

30. 2-Decarboxy-2-hydroxymethyl-16,16-difluoro-19,20-didehydro-PGF$_{1\beta}$, a compound according to claim 27.

31. A compound according to claim 20, wherein R$_2$ is hydroxymethyl.

32. A compound according to claim 31, wherein X is trans-CH=CH-.

33. 2-Decarboxy-2-hydroxymethyl-11-deoxy-11α-hydroxymethyl-19,20-didehydro-PGF$_{1\beta}$, a compound according to claim 32.

34. 2-Decarboxy-2-hydroxymethyl-11-deoxy-11α-hydroxymethyl-16,16-dimethyl-19,20-didehydro-PGF$_{1\beta}$, a compound according to claim 32.

35. 2-Decarboxy-2-hydroxymethyl-11-deoxy-11α-hydroxymethyl-16,16-difluoro-19,20-didehydro-PGF$_{1\beta}$, a compound according to claim 32.

36. A compound according to claim 3, wherein W is $$\overset{O}{\underset{\|}{}}$$

37. A compound according to claim 36, wherein R$_2$ is hydroxyl.

38. A compound according to claim 37, wherein X is trans-CH=CH-.

39. 2-Decarboxy-2-hydroxymethyl-19,20-didehydro-PGE$_1$, a compound according to claim 38.

40. 2-Decarboxy-2-hydroxymethyl-16,16-dimethyl-19,20-didehydro-PGE$_1$, a compound according to claim 38.

41. 2-Decarboxy-2-hydroxymethyl-16,16-difluoro-19,20-dihydro-PGE$_1$, a compound according to claim 38.

42. A compound according to claim 36, wherein R$_2$ is hydrogen.

43. A compound according to claim 42, wherein X is trans-CH=CH-.

44. 2-Decarboxy-2-hydroxymethyl-11-deoxy-19,20-didehydro-PGE$_1$, a compound according to claim 43.

45. 2-Decarboxy-2-hydroxymethyl-11-deoxy-16,16-dimethyl-19,20-didehydro-PGE$_1$, a compound according to claim 43.

46. 2-Decarboxy-2-hydroxymethyl-11-deoxy-16,16-difluoro-19,20-didehydro-PGE$_1$, a compound according to claim 43.

47. A compound according to claim 36, wherein R$_2$ is hydroxymethyl.

48. A compound according to claim 47, wherein X is trans-CH=CH-.

49. 2-Decarboxy-2-hydroxymethyl-11-deoxy-11α-hydroxymethyl-19,20-didehydro-PGE$_1$, a compound according to claim 48.

50. 2-Decarboxy-2-hydroxymethyl-11-deoxy-11α-hydroxymethyl-16,16-dimethyl-19,20-PGE$_1$, a compound according to claim 48.

51. 2-Decarboxy-2-hydroxymethyl-11-deoxy-11α-hydroxymethyl-16,16-difluoro-19,20-didehydro-PGE$_1$, a compound according to claim 48.

52. A compound according to claim 3, wherein W is $$\overset{CH_2}{\underset{\|}{}}$$

53. A compound according to claim 52, wherein R$_2$ is hydroxyl.

54. A compound according to claim 53, wherein X is trans-CH=CH-.

55. 2-Decarboxy-2-hydroxymethyl-9-deoxo-9-methylene-19,20-didehydro-PGE$_1$, a compound according to claim 54.

56. 2-Decarboxy-2-hydroxymethyl-9-deoxo-9-methylene-16,16-dimethyl-19,20-didehydro-PGE$_1$, a compound according to claim 54.

57. 2-Decarboxy-2-hydroxymethyl-9-deoxo-9-methylene-16,16-difluoro-19,20-didehydro-PGE$_1$, a compound according to claim 54.

58. A compound according to claim 52, wherein R$_2$ is hydrogen.

59. A compound according to claim 58, wherein X is trans-CH=CH-.

60. 2-Decarboxy-2-hydroxymethyl-9-deoxo-9-methylene-11-deoxy-19,20-didehydro-PGE$_1$, a compound according to claim 59.

61. 2-Decarboxy-2-hydroxymethyl-9-deoxo-9-methylene-11-deoxy-16,16-dimethyl-19,20-didehydro-PGE$_1$, a compound according to claim 59.

62. 2-Decarboxy-2-hydroxymethyl-9-deoxo-9-methylene-11-deoxy-16,16-difluoro-19,20-didehydro-PGE$_1$, a compound according to claim 59.

63. A compound according to claim 52, wherein R$_2$ is hydroxymethyl.

64. A compound according to claim 63, wherein X is trans-CH=CH-.

65. 2-Decarboxy-2-hydroxymethyl-9-deoxo-9-methylene-11-deoxy-11α-hydroxymethyl-19,20-didehydro-PGE$_1$, a compound according to claim 64.

66. 2-Decarboxy-2-hydroxymethyl-9-deoxo-9-methylene-11-deoxy-11α-hydroxymethyl-16,16-dimethyl-19,20-didehydro-PGE$_1$, a compound according to claim 64.

67. 2-Decarboxy-2-hydroxymethyl-9-deoxo-9-methylene-11-deoxy-11α-hydroxymethyl-16,16-difluoro-19,20-didehydro-PGE$_1$, a compound according to claim 64.

* * * * *

UNITED STATES PATENT OFFICE
CERTIFICATE OF CORRECTION

Patent No. 4,259,528         Dated 31 March 1981

Inventor(s) John C. Sih

It is certified that error appears in the above-identified patent and that said Letters Patent are hereby corrected as shown below:

Column 1, line 8, "pending issuance as a United States Patent" should read -- now United States Patent 4,243,611 --;

Column 1, lines 35-43 and Column 3, lines 35-43,

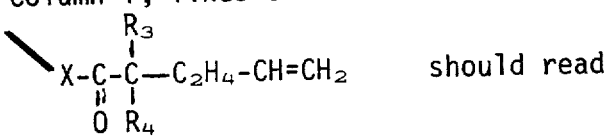   should read   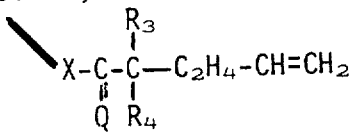

Column 2, line 36, "$PGF_1\alpha$" should read -- $PGF_1\beta$ --;
Column 4, lines 52, 55, and 58, "according to claim 15" should read -- according to claim 16 --.
Column 5, line 5, "according to claim 20" should read -- according to claim 22 --.

Signed and Sealed this

Sixth Day of October 1981

[SEAL]

Attest:

GERALD J. MOSSINGHOFF

Attesting Officer     Commissioner of Patents and Trademarks